(12) United States Patent
Metten et al.

(10) Patent No.: US 9,095,529 B2
(45) Date of Patent: *Aug. 4, 2015

(54) PRODUCT FOR TEMPORARILY SHAPING KERATIN FIBERS ON THE BASIS OF A COMBINATION OF SPECIFIC FILM-FORMING POLYMERS

(71) Applicant: Henkel AG & Co. KGaA, Dusseldorf (DE)

(72) Inventors: Diane Metten, Hamburg (DE); Bernd Richters, Hamburg (DE); Rene Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,831

(22) PCT Filed: Nov. 9, 2012

(86) PCT No.: PCT/EP2012/072277
§ 371 (c)(1),
(2) Date: Jun. 20, 2014

(87) PCT Pub. No.: WO2013/091995
PCT Pub. Date: Jun. 27, 2013

(65) Prior Publication Data
US 2015/0017113 A1    Jan. 15, 2015

(30) Foreign Application Priority Data

Dec. 20, 2011   (DE) .................... 10 2011 089 170

(51) Int. Cl.
*A61Q 5/06* (2006.01)
*A61K 8/81* (2006.01)

(52) U.S. Cl.
CPC ............. *A61K 8/8182* (2013.01); *A61K 8/8152* (2013.01); *A61Q 5/06* (2013.01); *A61K 2800/594* (2013.01)

(58) Field of Classification Search
CPC . A61Q 5/06; A61K 8/8182; A61K 2800/594; A61K 8/416
USPC .................. 424/70.13, 70.16, 70.28
See application file for complete search history.

(56) References Cited

U.S. PATENT DOCUMENTS

2003/0223948 A1* 12/2003 Maubru ................. 424/70.13
2009/0068136 A1*  3/2009 Beumer et al. .......... 424/70.16
2010/0129307 A1*  5/2010 Singer et al. ........... 424/70.13

FOREIGN PATENT DOCUMENTS

DE      102007053951 A1    5/2009
DE      102007053955 A1    5/2009
WO         0040628 A1     7/2000

OTHER PUBLICATIONS

International Search Report completed Aug. 14, 2013 in PCT/EP2012/072277.
Database GNPD, "Stand Tough Extreme Gel," Oct. 2011.
Database GNPD, "Volumizing Spray," Aug. 2010.
Database GNPD, "Styling Mould," Sep. 2008.

* cited by examiner

*Primary Examiner* — Eisa Elhilo
(74) *Attorney, Agent, or Firm* — P. Scott Smith

(57) ABSTRACT

A cosmetic agent, containing in a cosmetically acceptable carrier a) at least one copolymer (A) of allyl methacrylate with one or more monomers selected from acrylic acid, methacrylic acid, acrylic acid esters and methacrylic acid esters, b) at least one polymeric quaternary ammonium compound (B) from the group of vinylpyrrolidone copolymers, is provided for temporarily deforming keratinic fibers.

12 Claims, No Drawings

PRODUCT FOR TEMPORARILY SHAPING KERATIN FIBERS ON THE BASIS OF A COMBINATION OF SPECIFIC FILM-FORMING POLYMERS

CROSS REFERENCE TO RELATED APPLICATIONS

The present disclosure is a U.S. National Stage entry under 35 U.S.C. §371 based on International Application No. PCT/EP2012/072277, filed Nov. 9, 2012 which was published under PCT Article 21(2) and which claims priority to German Patent Application No. 10 2011 089 170.6 filed on Dec. 20, 2011, which is incorporated herein by reference in its entirety.

TECHNICAL FIELD

The technical field describes cosmetic agents based on a specific polymer combination, use of these cosmetic agents for temporarily deforming keratinic fibers and cosmetic methods using these agents.

BACKGROUND

Polymers are widely used in the most varied cosmetic agents. They are to be found in agents for treating skin as well as in agents for treating hair, in agents which are washed off or out again directly after use, i.e. "rinse-off products", and in agents which remain on the skin or hair, i.e. "leave-on agents". The polymers are used for the most varied reasons and specific properties of the polymers are exploited in each case. In agents for treating skin, in shampoos, hair rinses and hair masks, the emphasis often lies on the thickening or conditioning properties of the polymers. In agents for temporarily deforming keratinic fibers, hereinafter also known as styling agents, alongside these properties film-forming and/or setting effects are particularly desired. Polymers often also serve as auxiliaries for improving or indeed enabling deposition and fixing of other active substances and ingredients on the skin or hair. By adding suitable polymers to hair coloring agents, for example, rubbing fastness and coloring durability may be increased.

Cosmetic agents generally contain individual polymers which are specifically tailored to achieving a very specific effect. If various effects are to be achieved, a plurality of polymers must be added. However, using too many different polymers may be associated with a series of disadvantages. Problems may accordingly arise during formulation, for instance because the polymers react with one another or with other components of the agent resulting in precipitation or decomposition phenomena. Certain polymers also have a tendency to be deposited so permanently on the skin and in particular on the hair that they are no longer completely removed with normal washing and the polymer accumulates undesirably so ultimately leading to contamination of the skin or hair.

There is therefore a constant need for polymers or suitable combinations of small numbers of polymers which simultaneously exhibit as many as possible of the desired properties. For example, in the case of styling agents, the polymers used need to give the treated hair the strongest possible hold. In addition to a high degree of hold, styling agents must meet a whole series of further requirements. These may be broadly divided into properties on the hair, properties of the respective formulation, for example properties of the foam, the gel or the sprayed aerosol, and properties which affect the handling of the styling agent, wherein properties on the hair are of particular importance. Particular mention should be made of moisture resistance, low tackiness and a well-balanced conditioning effect. Moreover, a styling agent should as far as possible be universally applicable for all hair types. If the styling agent is a gel or a paste, the polymers should additionally have thickening properties.

Accordingly, it is desirable to provide further suitable polymer combinations which are distinguished by good film-forming and/or setting properties, have a very high level of hold without having to sacrifice flexibility and good moisture resistance, in particular perspiration and water resistance, and are additionally suitable for producing stably viscous and stably transparent cosmetic compositions.

SUMMARY

These objects were achieved by a specific polymer combination. An exemplary embodiment accordingly firstly provides a cosmetic agent, containing in a cosmetically acceptable carrier
a) at least one copolymer A of allyl methacrylate with one or more monomers selected from acrylic acid, methacrylic acid, acrylic acid esters and methacrylic acid esters
b) at least one polymeric quaternary ammonium compound B from the group of vinylpyrrolidone copolymers. In another embodiment, a method for temporarily deforming keratinic fibers is provided. The method includes applying onto the keratinic fibers a cosmetic agent, containing in cosmetically acceptable carrier
a) at least one copolymer A of allyl methacrylate with one or more monomers selected from acrylic acid, methacrylic acid, acrylic acid esters and methacrylic acid esters
b) at least one polymeric quaternary ammonium compound B from the group of vinylpyrrolidone copolymers.

DETAILED DESCRIPTION

Exemplary cosmetic agents contain the active substances in a cosmetic carrier. The cosmetic carrier is aqueous, alcoholic or aqueous-alcoholic. Exemplary aqueous-alcoholic carriers can be taken to be hydrous compositions containing from about 3 to about 70 wt. % of a $C_1$-$C_4$ alcohol, in particular ethanol or isopropanol, relative to the total weight of the mixture for use. For the purposes of the invention, an aqueous carrier contains at least about 30 wt. %, such as at least about 50 wt. % water, relative to the total weight of the mixture for use. Exemplary cosmetic agents contain, relative to the total weight thereof, from about 40 to about 99 wt. %, such as from about 50 to about 98 wt. %, for example from about 60 to about 95 wt. % or from about 70 to about 90 wt. % water. The pH value (10% solution, 20° C.) of exemplary cosmetic agents amounts to from about 4 to about 9, such as from about 5 to about 8, for example from about 6 to about 7.

Exemplary agents contain as first essential component a copolymer A of allyl methacrylate with one or more monomers selected from acrylic acid, methacrylic acid, acrylic acid esters and methacrylic acid esters.

Exemplary acrylic acid esters and methacrylic acid esters comprise $C_1$-$C_{12}$ alkyl acrylates and $C_1$-$C_{12}$ alkyl methacrylates, such as methyl acrylate, ethyl acrylate, propyl acrylate, methyl methacrylate, ethyl methacrylate, propyl methacrylate and mixtures thereof. In an exemplary embodiment, a copolymer A of allyl methacrylate is used with one or more monomers a1) selected from acrylic acid and methacrylic acid; and one or more monomers a1) selected from acrylic acid esters and methacrylic acid esters.

For the technical effect of exemplary agents, it has proven advantageous for the copolymer A to be based in a proportion of at least about 70 wt. %, such as of at least about 80 wt. %, for example of at least about 90 wt. % or at least about 95 wt. % on allyl methacrylate and one or more monomers from the group acrylic acid, methacrylic acid, acrylic acid esters and methacrylic acid esters.

An exemplary embodiment uses terpolymers, comprising
allyl methacrylate and
one or more monomers from the group acrylic acid, methacrylic acid and
one or more monomers from the group acrylic acid esters and methacrylic acid esters.

In an exemplary embodiment, the copolymer A is based in a proportion of at least about 70 wt. %, such as at least about 80 wt. %, for example at least about 90 wt. % or at least about 95 wt. % on
allyl methacrylate and
one or more monomers from the group acrylic acid, methacrylic acid and
one or more monomers from the group acrylic acid esters and methacrylic acid esters.

An exemplary copolymer A consists of the aminomethylpropanol salt of copolymers of allyl methacrylate with one or more monomers selected from acrylic acid, methacrylic acid, acrylic acid esters and methacrylic acid esters. A corresponding copolymer with the INCI name AMP-Acrylates/Allyl Methacrylate Copolymer is distributed by Noveon under the name Fixate™ G-100.

The proportion by weight of copolymer A in the total weight of exemplary cosmetic agents amounts to from about 0.05 to about 10 wt. %, such as from about 0.1 to about 7.0 wt. %, for example from about 0.2 to about 5.0 wt. %.

Exemplary agents contain as second essential component a polymeric quaternary ammonium compound from the group of vinylpyrrolidone copolymers B.

Suitable copolymers B are, for example,
quaternized vinylpyrrolidone/dimethylaminoethyl methacrylate copolymer (INCI name Polyquaternium-11), for example the copolymers with the trade names Gafquat® 755 N and Gafquat® 734 (GafCo., USA) and Luviquat PQ 11 PN (BASF);
vinylpyrrolidone/imidazolimine methochloride copolymer (INCI name Polyquaternium-16), for example the copolymer Luviquat® MQ 552 (BASF);
vinylpyrrolidone/methacrylamidopropyltrimethylammonium chloride copolymer (INCI name Polyquaternium-28), for example the copolymer Gafquat® HS 100 (ISP);
methylvinylimidazolium chloride/vinylpyrrolidone copolymer (INCI name Polyquaternium-44), for example Luviquat® Ultra Care (BASF);
quaternized vinylpyrrolidone/vinylcaprolactam/vinylimidazole copolymer (INCI name Polyquaternium-46), for example Luviquat® Hold (BASF);
quaternized vinylpyrrolidone/vinylcaprolactam/vinylimidazole/quaternized vinylimidazole copolymer (INCI name Polyquaternium-68), for example Luviquat® Supreme (BASF).

In an exemplary embodiment, the agent contains at least one copolymer B, selected from
b1) copolymers of vinylpyrrolidone with methacrylamidopropyltrimethylammonium chloride (MAPTAC) and/or
b2) copolymers of vinylpyrrolidone with dimethylaminoethyl methacrylate and/or
b3) copolymers of vinylpyrrolidone with dimethylaminopropylmethacrylamide and alkyldimethylpropylmethacrylamidoammonium salts.

Exemplary cosmetic agents are, for example, accordingly those which contain as copolymer B copolymers of vinylpyrrolidone with methacrylamidopropyltrimethylammonium chloride (MAPTAC) (b1).

These can be described by the general formula

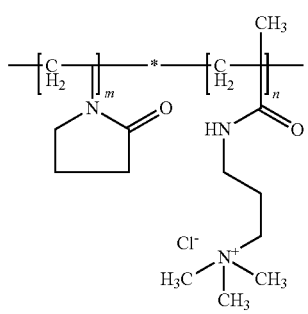

wherein the indices m and n vary depending on the molar mass of the polymer and are not intended to mean that the copolymers are block copolymers. Instead, structural units may be randomly distributed in the molecule.

Exemplary cosmetic agents are characterized in that they contain as cationic polymer b1 copolymers of methacrylamidopropyltrimethylammonium chloride (MAPTAC) with vinylpyrrolidone, which contain from about 40 to about 95 mol. %, such as from about 42.5 to about 90 mol. %, for example from about 45 to about 85 mol. % or from about 50 to about 80 mol. % vinylpyrrolidone.

Exemplary cosmetic agents are further characterized in that the copolymers b1 have molar masses of from about 10 to about 1000 kDA, such as of from about 25 to about 900 kDA, for example of from about 50 to about 800 kDA or of from about 100 to about 750 kDA.

An exemplary copolymer b1 is known according to INCI nomenclature as Polyquaternium-28. Such a polymer is obtainable for example under the trade name Gafquat® HS-100 (ISP).

In addition to the polymer(s) b1 or instead of the polymer(s) b1, the exemplary cosmetic agents may contain polymers b2 from the group of copolymers of vinylpyrrolidone with dimethylaminoethyl methacrylate.

These can be described by the general formula

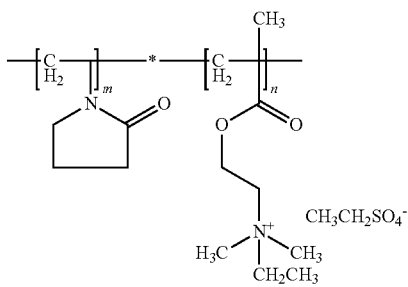

wherein the indices m and n vary depending on the molar mass of the polymer and are not intended to mean that the copolymers are block copolymers. Instead, structural units may be randomly distributed in the molecule.

Exemplary cosmetic agents are characterized in that they contain as cationic polymer b2 copolymers of vinylpyrrolidone with dimethylaminoethyl methacrylate, which contain from about 40 to about 95 mol. %, such as from about 42.5 to about 90 mol. %, for example from about 45 to about 85 mol. % or from about 50 to about 80 mol. % vinylpyrrolidone.

Exemplary cosmetic agents are further characterized in that the copolymers b2 have molar masses of from about 100 to about 2500 kDA, such as about 250 to about 2000 kDA, for example from about 500 to about 1750 kDA or from about 800 to about 1500 kDA.

An exemplary copolymer b2 is known according to INCI nomenclature as Polyquaternium-11. Such a polymer is obtainable for example under the trade name Gafquat® HS-755 (ISP).

In addition to the polymer(s) b1 and/or the polymer(s) b2 or instead of the polymer(s) b1 and/or the polymer(s) b2, the exemplary cosmetic agents may contain polymers b3 from the group of copolymers of vinylpyrrolidone with dimethylaminopropylmethacrylamide and alkyldimethylpropylmethacrylamidoammonium salts.

These can be described by the general formula

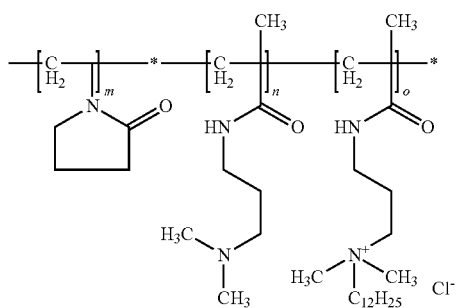

wherein the indices m, n and o vary depending on the molar mass of the polymer and are not intended to mean that the copolymers are block copolymers. Instead, structural units may be randomly distributed in the molecule.

Exemplary cosmetic agents are characterized in that they contain as cationic polymer b3 copolymers of vinylpyrrolidone with dimethylaminopropylmethacrylamide and lauryldimethylpropylmethacrylamidoammonium salts.

Exemplary cosmetic agents are further characterized in that they contain as cationic polymer b3 copolymers of vinylpyrrolidone with dimethylaminopropylmethacrylamide and alkyldimethylpropylmethacrylamidoammonium salts, which contain from about 40 to about 95 mol. %, such as from about 42.5 to about 90 mol. %, for example from about 45 to about 85 mol. % or from about 50 to about 80 mol. % vinylpyrrolidone.

Exemplary cosmetic agents are furthermore characterized in that the copolymers b3 have molar masses of from about 10 to about 1000 kDA, such as from about 25 to about 900 kDA, for example from about 50 to 800 kDA or from about 100 to about 750 kDA.

An exemplary copolymer b3 is known according to INCI nomenclature as Polyquaternium-55. Such a polymer is obtainable for example under the trade name Styleze® W20 (ISP).

For the cosmetic action of exemplary agents, vinylpyrrolidone/methacrylamidopropyltrimethylammonium chloride copolymers may be used, such as in exemplary cosmetic agents in which the copolymer B is selected from the group of copolymers of vinylpyrrolidone with methacrylamidopropyltrimethylammonium chloride. In particular, those copolymers B may be based in a proportion of at least about 70 wt. %, such as at least about 80 wt. %, for example at least about 90 wt. % or at least about 95 wt. % on vinylpyrrolidone and methacrylamidopropyltrimethylammonium chloride.

The proportion by weight of copolymer B in the total weight of exemplary cosmetic agents amounts to from about 0.05 to about 10 wt. %, such as from about 0.1 to about 7.0 wt. % or from about 0.2 to about 5.0 wt. %.

Exemplary agents are distinguished from cosmetic agents with alternative vinylpyrrolidone copolymers not only by the above-stated advantages but in particular also by an improved level of hold. Exemplary agents may have a weight ratio of polymers A and B in the cosmetic agent of from about 8:1 to about 1:8, such as from about 6:1 to about 1:6, for example from about 4:1 to about 1:4.

Exemplary copolymer A is used in the cosmetic agents in partially neutralized or neutralized form. In an exemplary embodiment, at least one alkanolamine is used for neutralization. The alkanolamines usable as an alkalizing agent may be selected from primary amines with a $C_2$-$C_6$ alkyl parent substance which bears at least one hydroxyl group. Exemplary alkanolamines are selected from the group formed from 2-aminoethan-1-ol (monoethanolamine), tris(2-hydroxyethyl)-amine(triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Exemplary alkanolamines are selected from the group 2-aminoethan-1-ol, 2-amino-2-methylpropan-1-ol and 2-amino-2-methylpropane-1,3-diol. 2-Amino-2-methylpropanol has proven to be a suitable neutralizing agent. Exemplary cosmetic agents contain at least one alkanolamine, such as 2-amino-2-methylpropanol. 2-Amino-2-methylpropanol is used in exemplary agents in a quantity that does not exceed the quantity needed to neutralize copolymer A. The quantities of 2-amino-2-methylpropanol used in exemplary agents amounts to from about 80 to about 100%, such as from about 90 to about 100% and for example from about 95 to about 100% of the quantity required for complete neutralization of copolymer A. In an exemplary embodiment, the proportion by weight of 2-amino-2-methylpropanol in the total weight of the cosmetic agent amounts to from about 0.1 to about 4.0 wt. %, such as from about 0.2 to about 3.0 wt. %, for example from about 0.5 to about 2.0 wt. %.

In addition to the previously described copolymers and carrier substances, exemplary cosmetic agents may contain further ingredients. The group of these further ingredients in particular includes cosmetically active auxiliary substances and additives.

Exemplary cosmetic agents contain at least one quaternary ammonium compound. Monomeric or polymeric active substances may be used as the quaternary ammonium compound.

From the plurality of possible monomeric quaternary ammonium compounds, the compounds from the groups:

trimethylalkylammonium halides;

ester quats quaternary imidazolines may be used in exemplary embodiments.

The group of trimethylalkylammonium halides includes the compounds of formula (Tkat1).

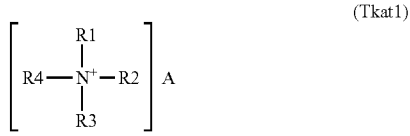
(Tkat1)

In the formula (Tkat1), R1, R2, R3 and R4 in each case mutually independently denote hydrogen, a methyl group, a phenyl group, a benzyl group, a saturated, branched or unbranched alkyl residue with a chain length of 8 to 30 carbon atoms, which may optionally be substituted with one or more hydroxyl groups. A denotes a physiologically acceptable anion, for example halides such as chloride or bromide and methosulfates. Examples of compounds of formula (Tkat1) are lauryltrimethylammonium chloride, cetyltrimethylammonium chloride, cetyltrimethylammonium bromide, cetyltrimethylammonium methosulfate, dicetyldimethylammonium chloride, tricetylmethylammonium chloride, stearyltrimethylammonium chloride, distearyldimethylammonium chloride, lauryldimethylbenzylammonium chloride, behenyltrimethylammonium chloride, behenyltrimethylammonium bromide and behenyltrimethylammonium methosulfate. Exemplary cosmetic agents contain a monomeric quaternary ammonium compound from the group of trimethylalkylammonium halides.

Further exemplary quaternary ammonium compounds are the cationic betaine esters of formula (Tkat1-2.1).

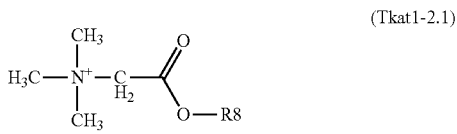
(Tkat1-2.1)

Exemplary ester quats are those with the trade names Armocare VGH-70, and Dehyquart® F-75, Dehyquart® L80, Stepantex® VS 90 and Akypoquat® 131.

A further group are quaternary imidazoline compounds. The formula (Tkat2) illustrated below shows the structure of these compounds.

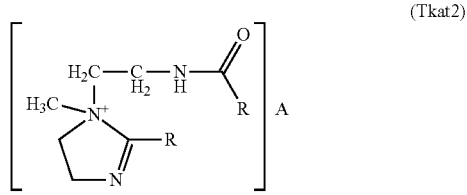
(Tkat2)

The residues R mutually independently in each case denote a saturated or unsaturated, linear or branched hydrocarbon residue with a chain length of 8 to 30 carbon atoms. Exemplary compounds of the formula (Tkat2) in each case contain the identical hydrocarbon residue for R. An exemplary chain length of the residues R amounts to 12 to 21 carbon atoms. A denotes an anion as previously described. Examples are obtainable under INCI names Quaternium-27, Quaternium-72, Quaternium-83, Quaternium-87 and Quaternium-91. In an exemplary embodiment, Quaternium-91 is used.

With regard to cosmetic action, exemplary cosmetic agents have a proportion by weight of the monomeric quaternary ammonium compound in the total weight of the agent amounting to from about 0.05 to about 3.0 wt. %, such as from about 0.1 to about 2.0 wt. %, for example from about 0.2 to about 1.0 wt. %.

Suitable auxiliary substances and additives which may be mentioned are in particular additional conditioning substances.

The agent may for example contain at least one protein hydrolysate and/or one of the derivatives thereof as a conditioning substance of another compound class. Protein hydrolysates are product mixtures which are obtained by acidically, basically or enzymatically catalyzed degradation of proteins. As used herein, the term protein hydrolysates also covers total hydrolysates and individual amino acids and the derivatives thereof and mixtures of different amino acids. The molecular weight of exemplary protein hydrolysates is from about 75, the molecular weight of glycine, to about 200,000 daltons, such as from about 75 to about 50,000 daltons, for example from about 75 to about 20,000 daltons.

An exemplary agent may furthermore contain at least one vitamin, a provitamin, a vitamin precursor and/or one of the derivatives thereof as a conditioning substance. Exemplary vitamins, provitamins and vitamin precursors a are those which are conventionally assigned to groups A, B, C, E, F and H.

Like the addition of glycerol and/or propylene glycol, the addition of panthenol may increase the flexibility of the polymer film formed using the exemplary agent.

Exemplary agents may furthermore contain at least one plant extract, and mono- or oligosaccharides and/or lipids as conditioning substance.

Oil bodies are furthermore suitable as a conditioning substance. Natural and synthetic cosmetic oil bodies include, for example, vegetable oils, liquid paraffin oils, isoparaffin oils and synthetic hydrocarbons and di-n-alkyl ethers having a total of between 12 to 36 C atoms, in particular 12 to 24 C atoms. Exemplary cosmetic agents contain at least one oil body, such as at least one oil body from the group of silicone oils. An exemplary group of silicone oils includes dimethicones, which also include cyclomethicones, amino-functional silicones and dimethiconols. The dimethicones may be both linear and branched and cyclic or cyclic and branched. Suitable silicone oils or silicone gums include dialkyl- and alkylarylsiloxanes, such as for example dimethylpolysiloxane and methylphenylpolysiloxane, and the alkoxylated, quaternized or also anionic derivatives thereof. Exemplary silicone oils or silicone gums include cyclic and linear polydialkylsiloxanes, the alkoxylated and/or aminated derivatives thereof, dihydroxypolydimethylsiloxanes and polyphenylalkylsiloxanes.

Ester oils, i.e. esters of $C_6$-$C_{30}$ fatty acids with $C_2$-$C_{30}$ fatty alcohols, such as monoesters of the fatty acids with alcohols with 2 to 24 C atoms such as for example isopropyl myristate (Rilanit® IPM), isononanoic acid $C_{16-18}$ alkyl esters (Cetiol® SN), 2-ethylhexyl palmitate (Cegesoft® 24), stearic acid 2-ethylhexyl ester, (Cetiol® 868), cetyl oleate, glycerol tricaprylate, coco fatty alcohol caprate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are further exemplary conditioning oil bodies.

Additional suitable conditioning substances are dicarboxylic acid esters, symmetrical, asymmetrical or cyclic esters of carbonic acid with fatty alcohols, trifatty acid esters of saturated and/or unsaturated linear and/or branched fatty acids with glycerol, or fatty acid partial glycerides, which should be understood to mean monoglycerides, diglycerides and the technical mixtures thereof.

With regard to cosmetic action, exemplary cosmetic agents are those in which the proportion by weight of the oil body in the total weight of the agent amounts to from about 0.01 to about 5.0 wt. %, such as from about 0.02 to about 4.0 wt. %, for example from about 0.05 to about 2.0 wt. %.

The following tables show the composition of some exemplary cosmetic agents (details in wt. % relative to the total weight of the cosmetic agent unless otherwise stated).

|  | Formula 1 | Formula 2 | Formula 3 | Formula 4 | Formula 5 |
|---|---|---|---|---|---|
| Copolymer A | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 6 | Formula 7 | Formula 8 | Formula 9 | Formula 10 |
|---|---|---|---|---|---|
| Copolymer A[1) | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 11 | Formula 12 | Formula 13 | Formula 14 | Formula 15 |
|---|---|---|---|---|---|
| Copolymer A | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 16 | Formula 17 | Formula 18 | Formula 19 | Formula 20 |
|---|---|---|---|---|---|
| Copolymer A[1) | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 21 | Formula 22 | Formula 23 | Formula 24 | Formula 25 |
|---|---|---|---|---|---|
| Copolymer A | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Alkanolamine[3) | 80 to 100 | 90 to 100 | 95 to 100 | 98 | 98 |
| Water, misc. | ad 100 | ad 100 | ad 100 | ad 100 | ad 100 |

|  | Formula 26 | Formula 27 | Formula 28 | Formula 29 | Formula 30 |
|---|---|---|---|---|---|
| Copolymer A[1) | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Alkanolamine[3) | 80 to 100 | 90 to 100 | 95 to 100 | 98 | 98 |
| Water, misc. | ad 100 | ad 100 | ad 100 | ad 100 | ad 100 |

|  | Formula 31 | Formula 32 | Formula 33 | Formula 34 | Formula 35 |
|---|---|---|---|---|---|
| Copolymer A | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| Alkanolamine[3) | 80 to 100 | 90 to 100 | 95 to 100 | 98 | 98 |
| Water, misc. | ad 100 | ad 100 | ad 100 | ad 100 | ad 100 |

|  | Formula 36 | Formula 37 | Formula 38 | Formula 39 | Formula 40 |
|---|---|---|---|---|---|
| Copolymer A[1) | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| Alkanolamine[3) | 80 to 100 | 90 to 100 | 95 to 100 | 98 | 98 |
| Water, misc. | ad 100 | ad 100 | ad 100 | ad 100 | ad 100 |

|  | Formula 41 | Formula 42 | Formula 43 | Formula 44 | Formula 45 |
|---|---|---|---|---|---|
| Copolymer A[1) | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| 2-Amino-2-methylpropanol[3) | 80 to 100 | 90 to 100 | 95 to 100 | 98 | 98 |
| Water, misc. | ad 100 | ad 100 | ad 100 | ad 100 | ad 100 |

|  | Formula 46 | Formula 47 | Formula 48 | Formula 49 | Formula 50 |
|---|---|---|---|---|---|
| Copolymer A[1) | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |
| Alkyltrimethyl-ammonium chloride | 0.05 to 3.0 | 0.1 to 2.0 | 0.2 to 1.0 | 0.5 | 0.3 |
| Water, misc. | ad 100 | ad 100 | ad 100 | ad 100 | ad 100 |

|  | Formula 51 | Formula 52 | Formula 53 | Formula 54 | Formula 55 |
|---|---|---|---|---|---|
| Copolymer A[1) | 0.05 to 10 | 0.1 to 7.0 | 0.2 to 5.0 | 0.4 | 1.2 |
| Copolymer B[2) | 0.05 to 10 | 0.1 to 7.0 | 0.2 to 5.0 | 0.8 | 0.8 |

-continued

|  | | | | | |
|---|---|---|---|---|---|
| Oil bodies | 0.01 to 5.0 | 0.02 to 4.0 | 0.05 to 2.0 | 0.1 | 0.1 |
| Water, misc. | ad 100 | ad 100 | ad 100 | ad 100 | ad 100 |

|  | Formula 56 | Formula 57 | Formula 58 | Formula 59 | Formula 60 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Water | 40 to 99 | 50 to 98 | 60 to 95 | 97 | 92 |
| Misc. | ad 100 | ad 100 | ad 100 | ad 100 | ad 100 |

|  | Formula 61 | Formula 62 | Formula 63 | Formula 64 | Formula 65 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Alkyltrimethyl-ammonium chloride | 0.05 to 3.0 | 0.1 to 2.0 | 0.2 to 1.0 | 0.5 | 0.3 |
| Water | 40 to 99 | 50 to 98 | 60 to 95 | 97 | 92 |
| Misc. | ad 100 | ad 100 | ad 100 | ad 100 | ad 100 |

|  | Formula 66 | Formula 67 | Formula 68 | Formula 69 | Formula 70 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Oil bodies | 0.01 to 5.0 | 0.02 to 4.0 | 0.05 to 2.0 | 0.1 | 0.1 |
| Water | 40 to 99 | 50 to 98 | 60 to 95 | 97 | 92 |
| Misc. | ad 100 | ad 100 | ad 100 | ad 100 | ad 100 |

|  | Formula 71 | Formula 72 | Formula 73 | Formula 74 | Formula 75 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| 2-Amino-2-methylpropanol[3] | 80 to 100 | 90 to 100 | 95 to 100 | 98 | 98 |
| Oil bodies | 0.01 to 5.0 | 0.02 to 4.0 | 0.05 to 2.0 | 0.1 | 0.1 |
| Water | 40 to 99 | 50 to 98 | 60 to 95 | 97 | 92 |
| Misc. | ad 100 | ad 100 | ad 100 | ad 100 | ad 100 |

[1] Copolymer A, which is based in a proportion of at least 95 wt. % on allyl methacrylate and one or more monomers from the group acrylic acid, methacrylic acid and one or more monomers from the group acrylic acid esters and methacrylic acid esters.
[2] Copolymer B, which is based in a proportion of at least about 95% on the monomers vinylpyrrolidone and methacrylamidopropyltrimethylammonium chloride
[3] % of the quantity required for complete neutralization of Copolymer A Exemplary cosmetic agents may be formulated in any forms conventional for cosmetic agents, for example in the form of solutions, which may for example be applied onto the hair as a hair lotion, in the form of creams, emulsions, waxes, gels or also surfactant-containing foaming solutions or other preparations which are suitable for use on the hair. In an alternative embodiment, these agents may however also assume gel or cream form, wherein transparent gels are more preferred.

Exemplary compositions are in particular highly suitable for stabilizing gas bubbles in the agent. In this way, air or other gases or gas mixtures can be readily incorporated into the exemplary agents in such a manner as to be stable in the long-term. This may optionally proceed during production of the agents, by exposing the agent to gas, preferably air, before packaging and packaging a product containing visible gas bubbles. The exemplary agents may assume the form of a foam. A foam is a preparation comprising gas filled bubbles surrounded by liquid (liquid foam) or solid (stiff foam) walls. The compositions listed in the following table are stiff foams in exemplary embodiments. The density of exemplary compositions amounts to from about 0.3 to about 1.0 g/cm$^3$, such as about 0.4 to about 0.9 g/cm$^3$, for example about 0.5 to about 0.8 g/cm$^3$. Such foams may for example be produced by beating the preparation in a suitable mixer or by exposure to a suitable gas, preferably air.

The following tables show the composition of some exemplary cosmetic foams. In this table the left-hand column ("formula x") refers in each case to one of the exemplary cosmetic compositions listed in the tables disclosed further above. The further columns two to seven ("density") in each case indicate the density of the corresponding cosmetic composition.

In other words, a cosmetic preparation according to line 12, column 5 of the following table comprises a cosmetic agent according to formula 11 with a density of 0.44 g/cm$^3$.

|  | Density [g/cm$^3$] | | | | | |
|---|---|---|---|---|---|---|
| Formula 1 | 0.3 to 1.0 | 0.93 | 0.4 to 0.9 | 0.44 | 0.5 to 0.8 | 0.61 |
| Formula 2 | 0.3 to 1.0 | 0.93 | 0.4 to 0.9 | 0.44 | 0.5 to 0.8 | 0.61 |
| Formula 3 | 0.3 to 1.0 | 0.93 | 0.4 to 0.9 | 0.44 | 0.5 to 0.8 | 0.61 |
| Formula 4 | 0.3 to 1.0 | 0.93 | 0.4 to 0.9 | 0.44 | 0.5 to 0.8 | 0.61 |
| Formula 5 | 0.3 to 1.0 | 0.93 | 0.4 to 0.9 | 0.44 | 0.5 to 0.8 | 0.61 |
| Formula 6 | 0.3 to 1.0 | 0.93 | 0.4 to 0.9 | 0.44 | 0.5 to 0.8 | 0.61 |
| Formula 7 | 0.3 to 1.0 | 0.93 | 0.4 to 0.9 | 0.44 | 0.5 to 0.8 | 0.61 |
| Formula 8 | 0.3 to 1.0 | 0.93 | 0.4 to 0.9 | 0.44 | 0.5 to 0.8 | 0.61 |
| Formula 9 | 0.3 to 1.0 | 0.93 | 0.4 to 0.9 | 0.44 | 0.5 to 0.8 | 0.61 |
| Formula 10 | 0.3 to 1.0 | 0.93 | 0.4 to 0.9 | 0.44 | 0.5 to 0.8 | 0.61 |
| Formula 11 | 0.3 to 1.0 | 0.93 | 0.4 to 0.9 | 0.44 | 0.5 to 0.8 | 0.61 |
| Formula 12 | 0.3 to 1.0 | 0.93 | 0.4 to 0.9 | 0.44 | 0.5 to 0.8 | 0.61 |
| Formula 13 | 0.3 to 1.0 | 0.93 | 0.4 to 0.9 | 0.44 | 0.5 to 0.8 | 0.61 |
| Formula 14 | 0.3 to 1.0 | 0.93 | 0.4 to 0.9 | 0.44 | 0.5 to 0.8 | 0.61 |
| Formula 15 | 0.3 to 1.0 | 0.93 | 0.4 to 0.9 | 0.44 | 0.5 to 0.8 | 0.61 |
| Formula 16 | 0.3 to 1.0 | 0.93 | 0.4 to 0.9 | 0.44 | 0.5 to 0.8 | 0.61 |
| Formula 17 | 0.3 to 1.0 | 0.93 | 0.4 to 0.9 | 0.44 | 0.5 to 0.8 | 0.61 |
| Formula 18 | 0.3 to 1.0 | 0.93 | 0.4 to 0.9 | 0.44 | 0.5 to 0.8 | 0.61 |
| Formula 19 | 0.3 to 1.0 | 0.93 | 0.4 to 0.9 | 0.44 | 0.5 to 0.8 | 0.61 |
| Formula 20 | 0.3 to 1.0 | 0.93 | 0.4 to 0.9 | 0.44 | 0.5 to 0.8 | 0.61 |
| Formula 21 | 0.3 to 1.0 | 0.93 | 0.4 to 0.9 | 0.44 | 0.5 to 0.8 | 0.61 |
| Formula 22 | 0.3 to 1.0 | 0.93 | 0.4 to 0.9 | 0.44 | 0.5 to 0.8 | 0.61 |
| Formula 23 | 0.3 to 1.0 | 0.93 | 0.4 to 0.9 | 0.44 | 0.5 to 0.8 | 0.61 |
| Formula 24 | 0.3 to 1.0 | 0.93 | 0.4 to 0.9 | 0.44 | 0.5 to 0.8 | 0.61 |
| Formula 25 | 0.3 to 1.0 | 0.93 | 0.4 to 0.9 | 0.44 | 0.5 to 0.8 | 0.61 |

| | Density [g/cm³] | | | | | |
|---|---|---|---|---|---|---|
| Formula 26 | 0.3 to 1.0 | 0.93 | 0.4 to 0.9 | 0.44 | 0.5 to 0.8 | 0.61 |
| Formula 27 | 0.3 to 1.0 | 0.93 | 0.4 to 0.9 | 0.44 | 0.5 to 0.8 | 0.61 |
| Formula 28 | 0.3 to 1.0 | 0.93 | 0.4 to 0.9 | 0.44 | 0.5 to 0.8 | 0.61 |
| Formula 29 | 0.3 to 1.0 | 0.93 | 0.4 to 0.9 | 0.44 | 0.5 to 0.8 | 0.61 |
| Formula 30 | 0.3 to 1.0 | 0.93 | 0.4 to 0.9 | 0.44 | 0.5 to 0.8 | 0.61 |
| Formula 31 | 0.3 to 1.0 | 0.93 | 0.4 to 0.9 | 0.44 | 0.5 to 0.8 | 0.61 |
| Formula 32 | 0.3 to 1.0 | 0.93 | 0.4 to 0.9 | 0.44 | 0.5 to 0.8 | 0.61 |
| Formula 33 | 0.3 to 1.0 | 0.93 | 0.4 to 0.9 | 0.44 | 0.5 to 0.8 | 0.61 |
| Formula 34 | 0.3 to 1.0 | 0.93 | 0.4 to 0.9 | 0.44 | 0.5 to 0.8 | 0.61 |
| Formula 35 | 0.3 to 1.0 | 0.93 | 0.4 to 0.9 | 0.44 | 0.5 to 0.8 | 0.61 |
| Formula 36 | 0.3 to 1.0 | 0.93 | 0.4 to 0.9 | 0.44 | 0.5 to 0.8 | 0.61 |
| Formula 37 | 0.3 to 1.0 | 0.93 | 0.4 to 0.9 | 0.44 | 0.5 to 0.8 | 0.61 |
| Formula 38 | 0.3 to 1.0 | 0.93 | 0.4 to 0.9 | 0.44 | 0.5 to 0.8 | 0.61 |
| Formula 39 | 0.3 to 1.0 | 0.93 | 0.4 to 0.9 | 0.44 | 0.5 to 0.8 | 0.61 |
| Formula 40 | 0.3 to 1.0 | 0.93 | 0.4 to 0.9 | 0.44 | 0.5 to 0.8 | 0.61 |
| Formula 41 | 0.3 to 1.0 | 0.93 | 0.4 to 0.9 | 0.44 | 0.5 to 0.8 | 0.61 |
| Formula 42 | 0.3 to 1.0 | 0.93 | 0.4 to 0.9 | 0.44 | 0.5 to 0.8 | 0.61 |
| Formula 43 | 0.3 to 1.0 | 0.93 | 0.4 to 0.9 | 0.44 | 0.5 to 0.8 | 0.61 |
| Formula 44 | 0.3 to 1.0 | 0.93 | 0.4 to 0.9 | 0.44 | 0.5 to 0.8 | 0.61 |
| Formula 45 | 0.3 to 1.0 | 0.93 | 0.4 to 0.9 | 0.44 | 0.5 to 0.8 | 0.61 |
| Formula 46 | 0.3 to 1.0 | 0.93 | 0.4 to 0.9 | 0.44 | 0.5 to 0.8 | 0.61 |
| Formula 47 | 0.3 to 1.0 | 0.93 | 0.4 to 0.9 | 0.44 | 0.5 to 0.8 | 0.61 |
| Formula 48 | 0.3 to 1.0 | 0.93 | 0.4 to 0.9 | 0.44 | 0.5 to 0.8 | 0.61 |
| Formula 49 | 0.3 to 1.0 | 0.93 | 0.4 to 0.9 | 0.44 | 0.5 to 0.8 | 0.61 |
| Formula 50 | 0.3 to 1.0 | 0.93 | 0.4 to 0.9 | 0.44 | 0.5 to 0.8 | 0.61 |
| Formula 51 | 0.3 to 1.0 | 0.93 | 0.4 to 0.9 | 0.44 | 0.5 to 0.8 | 0.61 |
| Formula 52 | 0.3 to 1.0 | 0.93 | 0.4 to 0.9 | 0.44 | 0.5 to 0.8 | 0.61 |
| Formula 53 | 0.3 to 1.0 | 0.93 | 0.4 to 0.9 | 0.44 | 0.5 to 0.8 | 0.61 |
| Formula 54 | 0.3 to 1.0 | 0.93 | 0.4 to 0.9 | 0.44 | 0.5 to 0.8 | 0.61 |
| Formula 55 | 0.3 to 1.0 | 0.93 | 0.4 to 0.9 | 0.44 | 0.5 to 0.8 | 0.61 |
| Formula 56 | 0.3 to 1.0 | 0.93 | 0.4 to 0.9 | 0.44 | 0.5 to 0.8 | 0.61 |
| Formula 57 | 0.3 to 1.0 | 0.93 | 0.4 to 0.9 | 0.44 | 0.5 to 0.8 | 0.61 |
| Formula 58 | 0.3 to 1.0 | 0.93 | 0.4 to 0.9 | 0.44 | 0.5 to 0.8 | 0.61 |
| Formula 59 | 0.3 to 1.0 | 0.93 | 0.4 to 0.9 | 0.44 | 0.5 to 0.8 | 0.61 |
| Formula 60 | 0.3 to 1.0 | 0.93 | 0.4 to 0.9 | 0.44 | 0.5 to 0.8 | 0.61 |
| Formula 61 | 0.3 to 1.0 | 0.93 | 0.4 to 0.9 | 0.44 | 0.5 to 0.8 | 0.61 |
| Formula 62 | 0.3 to 1.0 | 0.93 | 0.4 to 0.9 | 0.44 | 0.5 to 0.8 | 0.61 |
| Formula 63 | 0.3 to 1.0 | 0.93 | 0.4 to 0.9 | 0.44 | 0.5 to 0.8 | 0.61 |
| Formula 64 | 0.3 to 1.0 | 0.93 | 0.4 to 0.9 | 0.44 | 0.5 to 0.8 | 0.61 |
| Formula 65 | 0.3 to 1.0 | 0.93 | 0.4 to 0.9 | 0.44 | 0.5 to 0.8 | 0.61 |
| Formula 66 | 0.3 to 1.0 | 0.93 | 0.4 to 0.9 | 0.44 | 0.5 to 0.8 | 0.61 |
| Formula 67 | 0.3 to 1.0 | 0.93 | 0.4 to 0.9 | 0.44 | 0.5 to 0.8 | 0.61 |
| Formula 68 | 0.3 to 1.0 | 0.93 | 0.4 to 0.9 | 0.44 | 0.5 to 0.8 | 0.61 |
| Formula 69 | 0.3 to 1.0 | 0.93 | 0.4 to 0.9 | 0.44 | 0.5 to 0.8 | 0.61 |
| Formula 70 | 0.3 to 1.0 | 0.93 | 0.4 to 0.9 | 0.44 | 0.5 to 0.8 | 0.61 |
| Formula 71 | 0.3 to 1.0 | 0.93 | 0.4 to 0.9 | 0.44 | 0.5 to 0.8 | 0.61 |
| Formula 72 | 0.3 to 1.0 | 0.93 | 0.4 to 0.9 | 0.44 | 0.5 to 0.8 | 0.61 |
| Formula 73 | 0.3 to 1.0 | 0.93 | 0.4 to 0.9 | 0.44 | 0.5 to 0.8 | 0.61 |
| Formula 74 | 0.3 to 1.0 | 0.93 | 0.4 to 0.9 | 0.44 | 0.5 to 0.8 | 0.61 |
| Formula 75 | 0.3 to 1.0 | 0.93 | 0.4 to 0.9 | 0.44 | 0.5 to 0.8 | 0.61 |

In an alternative embodiment, exemplary cosmetic agents may be packaged as pump or aerosol sprays. In addition to further active and auxiliary substances, exemplary aerosol sprays contain a propellant. Exemplary suitable propellants (propellant gases) are propane, n-butane, iso-butane, dimethyl ether (DME), nitrogen, air, nitrous oxide, 1,1-difluoroethane, specifically both individually and in combination. Hydrophilic propellant gases, such as for example carbon dioxide, may also be used if a small proportion of hydrophilic gases is selected and a lipophilic propellant gas (for example propane/butane) is present in excess. Dimethyl ether, propane, n-butane, iso-butane and mixtures of these propellant gases are exemplary. In exemplary embodiments, propane/butane mixtures or isobutane are used. Exemplary cosmetic agents contain, relative to the total weight thereof, the propellant in a quantity of from about 2.0 to about 20 wt. %, such as from about 4.0 to about 15 wt. %, for example from about 5.0 to about 10 wt. %.

The following tables show the composition of some exemplary propellant-containing cosmetic agents. In this table the left-hand column ("formula x") refers in each case to one of the exemplary cosmetic compositions listed in the tables disclosed further above. The further columns two to seven ("propellant") in each case indicate the quantity of propellant added to the corresponding cosmetic composition. These indications in "wt. %" relate to the total weight of the cosmetic composition of the respective "formula x" without propellant.

In other words, a cosmetic preparation according to line 12, column 5 of the following table comprises a 20:1 mixture of the propellant-free cosmetic agent according to formula 11 with a propane/butane mixture.

| | Propellant [wt. %] | | | | | |
|---|---|---|---|---|---|---|
| Formula 1  | 2.0 to 10 | 5.0 | 2.0 to 10 P/B* | 5.0 P/B | 2.0 to 10 iB** | 5.0 iB |
| Formula 2  | 2.0 to 10 | 5.0 | 2.0 to 10 P/B* | 5.0 P/B | 2.0 to 10 iB** | 5.0 iB |
| Formula 3  | 2.0 to 10 | 5.0 | 2.0 to 10 P/B* | 5.0 P/B | 2.0 to 10 iB** | 5.0 iB |
| Formula 4  | 2.0 to 10 | 5.0 | 2.0 to 10 P/B* | 5.0 P/B | 2.0 to 10 iB** | 5.0 iB |
| Formula 5  | 2.0 to 10 | 5.0 | 2.0 to 10 P/B* | 5.0 P/B | 2.0 to 10 iB** | 5.0 iB |
| Formula 6  | 2.0 to 10 | 5.0 | 2.0 to 10 P/B* | 5.0 P/B | 2.0 to 10 iB** | 5.0 iB |
| Formula 7  | 2.0 to 10 | 5.0 | 2.0 to 10 P/B* | 5.0 P/B | 2.0 to 10 iB** | 5.0 iB |
| Formula 8  | 2.0 to 10 | 5.0 | 2.0 to 10 P/B* | 5.0 P/B | 2.0 to 10 iB** | 5.0 iB |
| Formula 9  | 2.0 to 10 | 5.0 | 2.0 to 10 P/B* | 5.0 P/B | 2.0 to 10 iB** | 5.0 iB |
| Formula 10 | 2.0 to 10 | 5.0 | 2.0 to 10 P/B* | 5.0 P/B | 2.0 to 10 iB** | 5.0 iB |
| Formula 11 | 2.0 to 10 | 5.0 | 2.0 to 10 P/B* | 5.0 P/B | 2.0 to 10 iB** | 5.0 iB |
| Formula 12 | 2.0 to 10 | 5.0 | 2.0 to 10 P/B* | 5.0 P/B | 2.0 to 10 iB** | 5.0 iB |
| Formula 13 | 2.0 to 10 | 5.0 | 2.0 to 10 P/B* | 5.0 P/B | 2.0 to 10 iB** | 5.0 iB |
| Formula 14 | 2.0 to 10 | 5.0 | 2.0 to 10 P/B* | 5.0 P/B | 2.0 to 10 iB** | 5.0 iB |
| Formula 15 | 2.0 to 10 | 5.0 | 2.0 to 10 P/B* | 5.0 P/B | 2.0 to 10 iB** | 5.0 iB |
| Formula 16 | 2.0 to 10 | 5.0 | 2.0 to 10 P/B* | 5.0 P/B | 2.0 to 10 iB** | 5.0 iB |
| Formula 17 | 2.0 to 10 | 5.0 | 2.0 to 10 P/B* | 5.0 P/B | 2.0 to 10 iB** | 5.0 iB |
| Formula 18 | 2.0 to 10 | 5.0 | 2.0 to 10 P/B* | 5.0 P/B | 2.0 to 10 iB** | 5.0 iB |
| Formula 19 | 2.0 to 10 | 5.0 | 2.0 to 10 P/B* | 5.0 P/B | 2.0 to 10 iB** | 5.0 iB |
| Formula 20 | 2.0 to 10 | 5.0 | 2.0 to 10 P/B* | 5.0 P/B | 2.0 to 10 iB** | 5.0 iB |
| Formula 21 | 2.0 to 10 | 5.0 | 2.0 to 10 P/B* | 5.0 P/B | 2.0 to 10 iB** | 5.0 iB |
| Formula 22 | 2.0 to 10 | 5.0 | 2.0 to 10 P/B* | 5.0 P/B | 2.0 to 10 iB** | 5.0 iB |
| Formula 23 | 2.0 to 10 | 5.0 | 2.0 to 10 P/B* | 5.0 P/B | 2.0 to 10 iB** | 5.0 iB |
| Formula 24 | 2.0 to 10 | 5.0 | 2.0 to 10 P/B* | 5.0 P/B | 2.0 to 10 iB** | 5.0 iB |
| Formula 25 | 2.0 to 10 | 5.0 | 2.0 to 10 P/B* | 5.0 P/B | 2.0 to 10 iB** | 5.0 iB |

-continued

| | | | Propellant [wt. %] | | | |
|---|---|---|---|---|---|---|
| Formula 26 | 2.0 to 10 | 5.0 | 2.0 to 10 P/B* | 5.0 P/B | 2.0 to 10 iB** | 5.0 iB |
| Formula 27 | 2.0 to 10 | 5.0 | 2.0 to 10 P/B* | 5.0 P/B | 2.0 to 10 iB** | 5.0 iB |
| Formula 28 | 2.0 to 10 | 5.0 | 2.0 to 10 P/B* | 5.0 P/B | 2.0 to 10 iB** | 5.0 iB |
| Formula 29 | 2.0 to 10 | 5.0 | 2.0 to 10 P/B* | 5.0 P/B | 2.0 to 10 iB** | 5.0 iB |
| Formula 30 | 2.0 to 10 | 5.0 | 2.0 to 10 P/B* | 5.0 P/B | 2.0 to 10 iB** | 5.0 iB |
| Formula 31 | 2.0 to 10 | 5.0 | 2.0 to 10 P/B* | 5.0 P/B | 2.0 to 10 iB** | 5.0 iB |
| Formula 32 | 2.0 to 10 | 5.0 | 2.0 to 10 P/B* | 5.0 P/B | 2.0 to 10 iB** | 5.0 iB |
| Formula 33 | 2.0 to 10 | 5.0 | 2.0 to 10 P/B* | 5.0 P/B | 2.0 to 10 iB** | 5.0 iB |
| Formula 34 | 2.0 to 10 | 5.0 | 2.0 to 10 P/B* | 5.0 P/B | 2.0 to 10 iB** | 5.0 iB |
| Formula 35 | 2.0 to 10 | 5.0 | 2.0 to 10 P/B* | 5.0 P/B | 2.0 to 10 iB** | 5.0 iB |
| Formula 36 | 2.0 to 10 | 5.0 | 2.0 to 10 P/B* | 5.0 P/B | 2.0 to 10 iB** | 5.0 iB |
| Formula 37 | 2.0 to 10 | 5.0 | 2.0 to 10 P/B* | 5.0 P/B | 2.0 to 10 iB** | 5.0 iB |
| Formula 38 | 2.0 to 10 | 5.0 | 2.0 to 10 P/B* | 5.0 P/B | 2.0 to 10 iB** | 5.0 iB |
| Formula 39 | 2.0 to 10 | 5.0 | 2.0 to 10 P/B* | 5.0 P/B | 2.0 to 10 iB** | 5.0 iB |
| Formula 40 | 2.0 to 10 | 5.0 | 2.0 to 10 P/B* | 5.0 P/B | 2.0 to 10 iB** | 5.0 iB |
| Formula 41 | 2.0 to 10 | 5.0 | 2.0 to 10 P/B* | 5.0 P/B | 2.0 to 10 iB** | 5.0 iB |
| Formula 42 | 2.0 to 10 | 5.0 | 2.0 to 10 P/B* | 5.0 P/B | 2.0 to 10 iB** | 5.0 iB |
| Formula 43 | 2.0 to 10 | 5.0 | 2.0 to 10 P/B* | 5.0 P/B | 2.0 to 10 iB** | 5.0 iB |
| Formula 44 | 2.0 to 10 | 5.0 | 2.0 to 10 P/B* | 5.0 P/B | 2.0 to 10 iB** | 5.0 iB |
| Formula 45 | 2.0 to 10 | 5.0 | 2.0 to 10 P/B* | 5.0 P/B | 2.0 to 10 iB** | 5.0 iB |
| Formula 46 | 2.0 to 10 | 5.0 | 2.0 to 10 P/B* | 5.0 P/B | 2.0 to 10 iB** | 5.0 iB |
| Formula 47 | 2.0 to 10 | 5.0 | 2.0 to 10 P/B* | 5.0 P/B | 2.0 to 10 iB** | 5.0 iB |
| Formula 48 | 2.0 to 10 | 5.0 | 2.0 to 10 P/B* | 5.0 P/B | 2.0 to 10 iB** | 5.0 iB |
| Formula 49 | 2.0 to 10 | 5.0 | 2.0 to 10 P/B* | 5.0 P/B | 2.0 to 10 iB** | 5.0 iB |
| Formula 50 | 2.0 to 10 | 5.0 | 2.0 to 10 P/B* | 5.0 P/B | 2.0 to 10 iB** | 5.0 iB |
| Formula 51 | 2.0 to 10 | 5.0 | 2.0 to 10 P/B* | 5.0 P/B | 2.0 to 10 iB** | 5.0 iB |
| Formula 52 | 2.0 to 10 | 5.0 | 2.0 to 10 P/B* | 5.0 P/B | 2.0 to 10 iB** | 5.0 iB |
| Formula 53 | 2.0 to 10 | 5.0 | 2.0 to 10 P/B* | 5.0 P/B | 2.0 to 10 iB** | 5.0 iB |
| Formula 54 | 2.0 to 10 | 5.0 | 2.0 to 10 P/B* | 5.0 P/B | 2.0 to 10 iB** | 5.0 iB |
| Formula 55 | 2.0 to 10 | 5.0 | 2.0 to 10 P/B* | 5.0 P/B | 2.0 to 10 iB** | 5.0 iB |
| Formula 56 | 2.0 to 10 | 5.0 | 2.0 to 10 P/B* | 5.0 P/B | 2.0 to 10 iB** | 5.0 iB |
| Formula 57 | 2.0 to 10 | 5.0 | 2.0 to 10 P/B* | 5.0 P/B | 2.0 to 10 iB** | 5.0 iB |
| Formula 58 | 2.0 to 10 | 5.0 | 2.0 to 10 P/B* | 5.0 P/B | 2.0 to 10 iB** | 5.0 iB |
| Formula 59 | 2.0 to 10 | 5.0 | 2.0 to 10 P/B* | 5.0 P/B | 2.0 to 10 iB** | 5.0 iB |
| Formula 60 | 2.0 to 10 | 5.0 | 2.0 to 10 P/B* | 5.0 P/B | 2.0 to 10 iB** | 5.0 iB |
| Formula 61 | 2.0 to 10 | 5.0 | 2.0 to 10 P/B* | 5.0 P/B | 2.0 to 10 iB** | 5.0 iB |
| Formula 62 | 2.0 to 10 | 5.0 | 2.0 to 10 P/B* | 5.0 P/B | 2.0 to 10 iB** | 5.0 iB |
| Formula 63 | 2.0 to 10 | 5.0 | 2.0 to 10 P/B* | 5.0 P/B | 2.0 to 10 iB** | 5.0 iB |
| Formula 64 | 2.0 to 10 | 5.0 | 2.0 to 10 P/B* | 5.0 P/B | 2.0 to 10 iB** | 5.0 iB |
| Formula 65 | 2.0 to 10 | 5.0 | 2.0 to 10 P/B* | 5.0 P/B | 2.0 to 10 iB** | 5.0 iB |
| Formula 66 | 2.0 to 10 | 5.0 | 2.0 to 10 P/B* | 5.0 P/B | 2.0 to 10 iB** | 5.0 iB |
| Formula 67 | 2.0 to 10 | 5.0 | 2.0 to 10 P/B* | 5.0 P/B | 2.0 to 10 iB** | 5.0 iB |
| Formula 68 | 2.0 to 10 | 5.0 | 2.0 to 10 P/B* | 5.0 P/B | 2.0 to 10 iB** | 5.0 iB |
| Formula 69 | 2.0 to 10 | 5.0 | 2.0 to 10 P/B* | 5.0 P/B | 2.0 to 10 iB** | 5.0 iB |
| Formula 70 | 2.0 to 10 | 5.0 | 2.0 to 10 P/B* | 5.0 P/B | 2.0 to 10 iB** | 5.0 iB |
| Formula 71 | 2.0 to 10 | 5.0 | 2.0 to 10 P/B* | 5.0 P/B | 2.0 to 10 iB** | 5.0 iB |
| Formula 72 | 2.0 to 10 | 5.0 | 2.0 to 10 P/B* | 5.0 P/B | 2.0 to 10 iB** | 5.0 iB |
| Formula 73 | 2.0 to 10 | 5.0 | 2.0 to 10 P/B* | 5.0 P/B | 2.0 to 10 iB** | 5.0 iB |
| Formula 74 | 2.0 to 10 | 5.0 | 2.0 to 10 P/B* | 5.0 P/B | 2.0 to 10 iB** | 5.0 iB |
| Formula 75 | 2.0 to 10 | 5.0 | 2.0 to 10 P/B* | 5.0 P/B | 2.0 to 10 iB** | 5.0 iB |

*"P/B" corresponds to a propane/butane mixture
**"iB" corresponds to isobutane

As explained above, exemplary agents have advantageous hair-fixing properties. The disclosure also provides a method for temporarily deforming keratinic fibers, in which a composition is applied onto the keratinic fibers. The disclosure also provides use of a cosmetic agent for temporarily deforming keratinic fibers. As explained above, exemplary agents are distinguished by improved hold in the case of temporary deformation of keratinic fibers. Exemplary embodiments provide the use of a cosmetic agent to improve hold in the case of temporary deformation of keratinic fibers.

Examples

The humidity resistance (High Humidity Curl Retention; HHCR) of the temporary hair deformation achieved using the following three hair cosmetic agents was determined

| | Invention 1 | Comparison 1 | Comparison 2 |
|---|---|---|---|
| Fixate G-100[1] | 2.90 | 5.77 | — |
| Gafquat HS-100[2] | 3.75 | — | 7.5 |
| Sodium benzoate | 0.3 | 0.3 | 0.3 |
| D-Panthenol (75%) | 0.2 | 0.2 | 0.2 |
| Dow Corning 939[3] | 0.2 | 0.2 | 0.2 |
| Dehyquart A CA[4] | 1.0 | 1.0 | 1.0 |
| Castor Oil, hydrogenated, 40 EO | 0.2 | 0.2 | 0.2 |
| Perfume | 0.1 | 0.1 | 0.1 |
| Water, misc. | ad 100 | ad 100 | ad 100 |

[1]Copolymer with the INCI name AMP-Acrylates/Allyl Methacrylate Copolymer (26% in water)
[2]Vinylpyrrolidone/methacrylamidopropyltrimethylammonium chloride copolymer (INCI: Polyquaternium-28, 20% in water)
[3]Silicone preparation (INCI: Amodimethicone, Trideceth-12, Cetrimonium Chloride)
[4]Trimethylhexadecylammonium chloride To determine High Humidity Curl Retention, standardized strands of hair from Kerling (item no. 827560) of the "European Natural" hair type, color 6/0, of a length ($L_{max}$) of 220 mm and a weight of 0.6 g were used. The strands were washed with a 12.5 wt. % sodium laureth sulfate solution by way of preparation. The strands of hair were dried overnight in a drying oven at 318 K.

0.18 g of the compositions were applied onto a strand of hair and rubbed in. The strand was then wound onto a curler (Fripac-medis, diameter 7 mm, item no. D-1203) and dried overnight at room temperature.

The curlers were carefully removed and the strands hung up. The length of the curls were in each case measured ($L_0$) and the strands placed in a conditioning cabinet. They were stored there at 294 K and a relative atmospheric humidity of 85% over a period of 6 h, after which the length of the curls was remeasured ($L_t$).

Five test strands per composition were correspondingly treated and measured.

High Humidity Curl Retention (HHCR) was calculated according to the following formula and the arithmetic mean of the HHCR values for the 5 test strands was determined for each composition:

$$HHCR = \frac{L_{max} - L_t}{L_{max} - L_0}$$

|      | Invention 1 | Comparison 1 | Comparison 2 |
| --- | --- | --- | --- |
| HHCR | 81% | 53% | 38% |

The measurement data reveal the synergistic action of the polymer combination according to the invention in composition Invention 1.

The invention claimed is:

1. A cosmetic agent, containing in a cosmetically acceptable carrier
   a) 0.05 to about 10 wt % of at least one copolymer A of allyl methacrylate with one or more monomers selected from acrylic acid, methacrylic acid, acrylic acid esters and methacrylic acid esters
   b) 0.05 to about 10 wt % of at least one polymeric quaternary ammonium compound B from the group of vinylpyrrolidone copolymers, and
   c) a monomeric quaternary ammonium compound from the group of trimethyl alkylammonium halides.

2. The cosmetic agent according to claim 1, containing in a cosmetically acceptable carrier at least one copolymer A of allyl methacrylate with
   one or more monomers a1) selected from acrylic acid and methacrylic acid; and
   one or more monomers a1) selected from acrylic acid esters and methacrylic acid esters.

3. The cosmetic agent according to claim 1, characterized in that the proportion by weight of copolymer A in the total weight of the agent amounts to from about 0.1 to about 7.0 wt. %.

4. The cosmetic agent according to claim 1, characterized in that the proportion by weight of copolymer A in the total weight of the agent amounts to from about 0.2 to about 5.0 wt. %.

5. The cosmetic agent according to claim 1, characterized in that copolymer B is selected from the group of copolymers of vinylpyrrolidone with methacrylamidopropyltrimethylammonium chloride.

6. The cosmetic agent according to claim 1, characterized in that the proportion by weight of copolymer B in the total weight of the agent amounts to from about 0.1 to about 7.0 wt. %.

7. The cosmetic agent according to claim 1, characterized in that the proportion by weight of copolymer B in the total weight of the agent amounts to from about 0.2 to about 5.0 wt. %.

8. The cosmetic agent according to claim 1, characterized in that the cosmetic agent furthermore contains at least one alkanolamine.

9. The cosmetic agent according to claim 1, characterized in that the cosmetic agent furthermore contains 2-amino-2-methylpropanol.

10. The cosmetic agent according to one claim 1, characterized in that it furthermore contains at least one oil body.

11. The cosmetic agent according to one claim 1, characterized in that it furthermore contains at least one oil body from the group of silicone oils.

12. A method for temporarily deforming keratinic fibers, the method comprising applying onto the keratinic fibers a cosmetic agent, containing in a cosmetically acceptable carrier
   a) 0.05 to about 10 wt % of at least one copolymer A of allyl methacrylate with one or more monomers selected from acrylic acid, methacrylic acid, acrylic acid esters and methacrylic acid esters
   b) 0.05 to about 10 wt % of at least one polymeric quaternary ammonium compound B from the group of vinylpyrrolidone copolymers and
   c) a monomeric quaternary ammonium compound from the group of trimethyl alkylammonium halides.

* * * * *